United States Patent [19]

Couillard et al.

[11] Patent Number: 5,483,334
[45] Date of Patent: Jan. 9, 1996

[54] SYSTEM FOR GENERATING THE SAME INSTANTANEOUS PRESSURE BETWEEN TWO TANKS

[75] Inventors: François Couillard, Yerres; Didier Frot, Choisy le Roi, both of France

[73] Assignee: Institut Francais du Petrole, Rueil-Malmaison, France

[21] Appl. No.: 277,019

[22] Filed: Jul. 19, 1994

[30] Foreign Application Priority Data

Jul. 19, 1993 [FR] France ................................ 93 08935

[51] Int. Cl.$^6$ .......................... G01N 21/33; G01N 21/45
[52] U.S. Cl. .................. 356/246; 250/373; 356/130; 356/246; 356/361; 356/411
[58] Field of Search ................................. 356/244, 246, 356/411, 440, 361, 130, 131, 132; 250/373

[56] References Cited

U.S. PATENT DOCUMENTS

| | | | |
|---|---|---|---|
| 2,857,803 | 10/1958 | Reinecke et al. | 356/246 |
| 3,035,482 | 5/1962 | Kinder | 356/361 X |
| 4,571,078 | 2/1986 | Capps, II | 356/246 |
| 5,173,742 | 12/1992 | Young | 356/440 X |

FOREIGN PATENT DOCUMENTS

| | | | |
|---|---|---|---|
| 552401 | 1/1958 | Canada | 356/361 |
| 0239487 | 9/1987 | European Pat. Off. . | |
| 1322957 | 2/1963 | France . | |

OTHER PUBLICATIONS

Database WPI, Week 8601, Jan. 21, 1986.

*Primary Examiner*—Vincent P. McGraw
*Attorney, Agent, or Firm*—Antonelli, Terry, Stout & Kraus

[57] ABSTRACT

The present invention relates to a system for generating the same instantaneous pressure between two tanks filled each with a given medium, the first tank including at least one inlet channel and at least one outlet channel for the given medium, the second tank including at least one outlet channel, and means for opening and for closing said channels. The system according to the invention further includes at least one linking capillary between each tank, intended notably for transmitting instantaneously a pressure variation from the first tank towards the second tank.

9 Claims, 1 Drawing Sheet

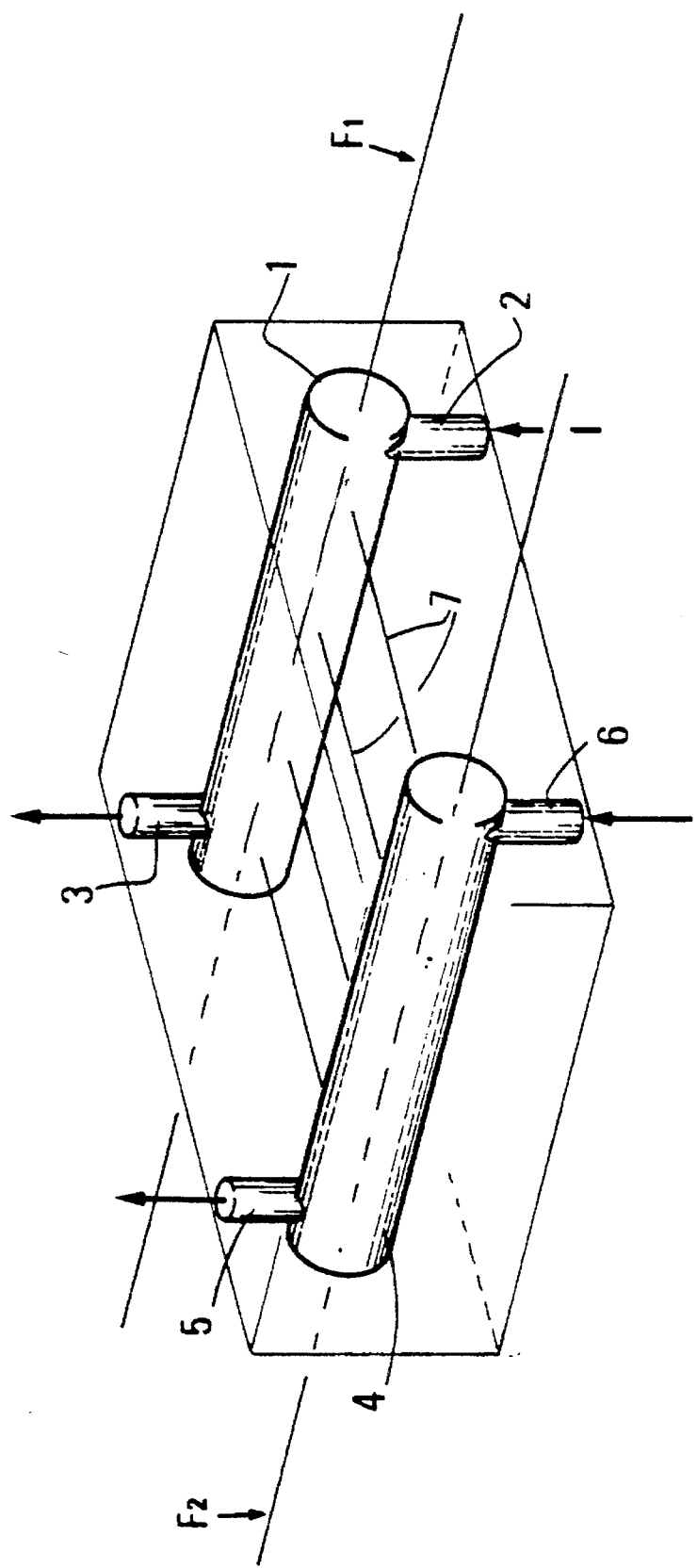

SYSTEM FOR GENERATING THE SAME INSTANTANEOUS PRESSURE BETWEEN TWO TANKS

FIELD OF THE INVENTION

The present invention relates to the field of media analysis by means of some of their physical properties.

More precisely, the invention relates to the field of the refractive index measurement of several media.

It may also be applied to photometry or to spectrophotometry.

BACKGROUND OF THE INVENTION

In these various fields, the detectors used commonly consist of at least two tanks. One tank, called the reference tank, contains a perfectly identified "control" medium, whereas a (generally liquid) medium certain properties of which vary according to its composition and which is to be analyzed circulates in the other tank.

High performance liquid chromatographs most often utilize these types of detectors, be they photometric, refractometric or spectrophotometric.

Photometers are advantageous in that they afford a great sensitivity and a high stability. They may be used in all the cases in which the eluates to be detected absorb the light within the wavelengths ranging between 190 and 700 nm. However, these photometers have major drawbacks: they are not universal and, in the same analysis, it is possible to meet with eluates which absorb the light at different wavelengths or which even do practically not absorb it, which entails the drawback of letting impurities go unnoticed, notably in preparative chromatography.

Moreover, in the case of preparative chromatography, the photometer is rapidly saturated around an optical density of the order of two.

This drawback may be decreased by dividing for example the length of the optical path in the tank by ten, but this entails a further loss of sensitivity.

The main advantage of refractometers is that they are practically universal. Most of the devices which are currently marketed are light beam deviation through double prismatic circulating vessel refractometers. In these detectors, a light source casts a beam onto a double photodetector after passing successively through a diaphragm, possibly concentrating lenses, a rotating glass strip with parallel faces for adjusting the optical zero of the device, i.e. for balancing the light intensity lighting up the two photodetectors, a double prismatic tank, one for a reference liquid and the other for the phase to be analyzed.

When the refractive index of the latter varies, the prismatic section of the two successive tanks is such that the beam deviates from one photodetector towards the other, according to the sign of the difference of the indexes between the two tanks. However, in some cases, notably in preparative chromatography, where high concentrations may be found in one of the two tanks, or if an elution gradient is created, the index variations may be such that the beam may deviate to the point of saturation of the device, which means that the deviated beam eventually only lights up one of the two cells. The chromatogram is thus clipped and several peaks with a common base may no longer be distinguished.

As it is the case for photometers, these drawbacks may be decreased by reducing the deviations, but here again at the expense of a sensitivity loss. Saturation is then avoided, but the smaller peaks, i.e. impurities, are no longer distinguished in preparative chromatography.

A refractometric system with a monochromatic source has also been proposed, whose beam is divided to pass through two tanks in parallel, for a reference liquid and the phase to be analyzed, then the two beams are reassembled to light up a photodetector. Interferences occur because of the variation of the optical path, on the measurement side, as a function of the index variation. One may consider that the sinusoid followed by the intensity is linear in the neighborhood of the index difference.

Document FR-2,596,526 describes an interferential differential refractometer in which each of the tanks, the reference and the measuring tank, takes independantly part in two independant interferometry systems but is "supplied" with light by the same source (laser for example).

The photometric detection of the two interferometers is performed by two independant photodetectors. It is understandable that, in such a system, each photodetector receives a light intensity which is a sinusoidal function of the difference of the refractive indexes between the reference tank and the measuring tank.

Consequently, if the refractive index varies progressively in very large proportions in one of the tanks, for example in gradient, the corresponding photodetector receives a light intensity of sinusoidal variation, which means that one has a phase information between the measuring and the reference tank which will depend, to within 2k, on the refractive index difference between the two tanks.

If this difference becomes very great, no change occurs, and the instrument, at the detection stage, never reaches saturation point. It is thus possible to refer to infinite measuring dynamics, although the refractive index is a finite quantity.

It has been noticed, for all the differential detectors that have been described, which include notably a measuring tank and a reference tank, that measurings are disturbed by the pressure variations in the tanks.

These pressure variations are due to the fact that the pumps used for circulating the liquid or mobile phase in the chromatography columns are not perfect and some pumps deliver particularly pulsed and unstable flow rates.

Now, it is known that the refractive index of a fluid depends on its density, and therefore on its pressure.

As a consequence of this dependance between pressure and refractive index, these detectors are difficult to use for high sensitivity operations, since flow rate irregularities due to the pumps generate detection signals which become higher than the sought signals.

Thus, in the known differential refractometers, a flow rate variation, and therefore a pressure variation, affects only the measuring tank since, in the reference tank, the medium is not stressed from outside. This variation, which is in no way compensated by the reference tank, causes an undesirable measuring signal.

Differential spectrophotometers are also affected by this problem, although more indirectly.

The working principle of spectrophotometers is in fact based on the absorption of the ultraviolet light by the products to be analyzed. However, the light beams passing through the reference tank and the measuring tank being not perfectly parallel, part of this light gets lost on the walls of the tank and this loss varies with the refractive index variations of the liquid.

Although the disturbance is lower than in the case of differential refractometers, it still remains a hindrance, notably during high sensitivity operations with low-performance pumps.

SUMMARY OF THE INVENTION

The present invention allows notably this problem to be solved by proposing a system capable of transmitting instantaneously a pressure from a first tank towards a second tank. In other words, the same instantaneous pressure is obtained in the two tanks concerned.

The aim of the present invention is to provide a system for generating the same instantaneous pressure between two tanks filled each with a given medium, the first tank including at least one inlet channel and at least one outlet channel, the second tank including at least one outlet channel, the system further comprising means for opening and for closing said channels.

According to the invention, the system includes at least one linking capillary between each tank, intended notably for transmitting instantaneously a pressure variation from one of the tanks towards the other tank.

More precisely, the first tank is a measuring tank in which the mobile phase to be analyzed flows, and the second tank is a tank containing a reference medium kept in the static state while measuring.

According to an embodiment of the invention, the linking capillary (or capillaries) allow the second tank to be filled.

According to another embodiment, the second tank also includes at least one inlet channel.

The system according to the invention may be used to measure refractive indexes in two different media.

Without departing from the scope of the invention, the system may also be used to measure the absorption of the ultraviolet light by the media present in the tanks.

According to another one of the aspects thereof, the invention may be used to measure the absorption of the visible light by the media present in each tank.

BRIEF DESCRIPTION OF THE DRAWING

The invention will be clear from reading the following description given by way of non limitative examples, with reference to the sole FIGURE appended.

This FIGURE diagrammatically shows the object of the present invention.

DESCRIPTION OF THE PREFERRED EMBODIMENTS

A first tank 1 called the measuring tank is crossed right through by a first light beam F1. It is fitted with at least one inlet channel 2 and with at least one outlet channel 3 for the medium to be analyzed.

A second tank 4, called the reference tank, is crossed by a second light beam F2. Tank 4 includes at least one outlet channel 5.

The second tank 4 may preferably, but not necessarily, be provided with an inlet channel 6.

Of course, means (not shown) capable of closing or not the channels, according to the working phases, are provided on each of the inlet channels 2 and outlet channels 3, 5.

If no channel is provided for feeding the second tank 4, one or several capillary channels 7 connecting the first tank 1 to the second tank 4 may be used as a feed (or inlet) channel for the reference medium.

The drawback of this solution lies in the low flow rate, and therefore in the difficulty in carrying off the bubbles during the filling of the second tank 4.

Apart from the feeding purpose described above, the purpose of the capillary channel(s) 7 is to transmit the pressure from one tank towards the other tank instantaneously.

Whether the invention is used for measuring refractive indexes or for photometric or spectrophotometric measurements, the working principle remains substantially the same.

The reference tank 4 is filled with a given medium, via capillaries 7 or via one or several specific feed channels 6. The medium it contains is static, in the sense that it does not flow in tank 4 during the measuring operation itself.

The medium to be analyzed flows in measuring tank 1. One or several pumps allow the medium to be pumped into tank 1. Tanks 1, 4 are each crossed by a beam F1, F2, respectively, disturbances in the beams providing give information on the composition to be analyzed.

Now, as stated above, the beam "disturbances" must only concern the parameters (refractive index, light absorption, etc) necessary for determining the composition.

The measuring quality and accuracy depend thereon.

The present invention, by proposing the improvement described above, is not adversely affected by measurement interferences, particularly by the pressure variations due to pumps conveying the medium into tank(s) 1, 4 and which have repercussions in the tank.

The capillary or capillaries 7 according to the invention allow this problem to be solved in a simple and reliable way, without any effect on the measuring accuracy.

Particularly, no significant pressure drop may be created by capillaries 7 since they generate almost no flow rate, in any way no flow rate likely to disturb the measurement.

In fact, in view of the compressibility of the liquids as a function of the pressure which is of the order of $1.10^{-4}$ bar$^{-1}$, and since the pressure variations (of the pumps) are commonly of the order of some millibars, the flow rate in the capillaries cannot generate any significant pressure drop therein.

The capillary diameter must be as small as possible. It will be a compromise between the (technical) achievement difficulties and the problems of diffusion of the eluates from measuring tank 1 towards reference tank 4.

Besides, it is possible, by means of the various valves provided (but not shown) on the inlet and outlet channels of the tanks, to perform, at the beginning of each analysis cycle, a complete draining of the reference tank so as to fill it with a totally pure and known phase.

In fact, in chromatography, in spite of the low flow rate in the capillaries, slow drifts due to the successive diffusions of the eluates towards reference tank 4 may occur.

Of course, the system which has been described may be provided with various additions and/or modifications by the man skilled in the art without departing from the scope of the present invention.

We claim:

1. A media analysis system for determining properties of different media and for generating the same instantaneous pressure between two tanks, each filled with a given medium, said system comprising a first tank containing a medium to be analyzed and including at least one inlet channel and at least one outlet channel for allowing passage of the medium therethrough, a second tank containing a reference medium and including at least one outlet channel for discharge of the reference medium, means for opening and closing said channels, and at least one linking capillary extending between and connected to the first tank and to the second tank for transmitting instantaneously a pressure variation in the medium to be analyzed from the first tank to the reference medium in the second tank, whereby variations in the analysis of the medium to be analyzed due to pressure variations in the first tank are avoided.

2. A system according to claim 1, further comprising at least one pump for pumping the medium to be analyzed into the first tank.

3. A system as claimed in claim 2, wherein the first tank comprises a measuring tank in which the medium to be analyzed flows and the second tank comprises a tank containing the reference medium kept in a static state during each measuring operation.

4. A system according to claim 1, wherein the at least one linking capillary provides means for filling the second tank.

5. A system according to claim 1, wherein the second tank further comprises at least one inlet channel.

6. A system according to claim 1, further comprising means for measuring refractive indexes of the medium in the first tank and the medium in the second tank.

7. A system according to claim 1, further comprising means for analyzing the medium in the first tank by liquid chromatography.

8. A system according to claim 1, further comprising means for measuring the absorption of ultraviolet light by the media present in each tank.

9. A system according to claim 1, further comprising means for measuring the absorption of visible light by the media present in each of said tanks.

* * * * *